United States Patent [19]

Okada et al.

[11] Patent Number: 5,202,352
[45] Date of Patent: Apr. 13, 1993

[54] INTRAVASCULAR EMBOLIZING AGENT CONTAINING ANGIOGENESIS-INHIBITING SUBSTANCE

[75] Inventors: Hiroaki Okada, Suita; Shigeru Kamei, Takarazuka; Toshio Yoshioka, Nishinomiya, all of Japan

[73] Assignee: Takeda Chemical Industries, Ltd., Osaka, Japan

[21] Appl. No.: 740,849

[22] Filed: Aug. 6, 1991

[51] Int. Cl.$^5$ .................... A61K 31/00; A61K 31/335
[52] U.S. Cl. ................................... 514/475; 514/492; 514/762; 514/763; 514/770; 514/787; 514/788.1
[58] Field of Search ............... 514/475, 492, 762, 763, 514/770, 787, 788.1

[56] References Cited

U.S. PATENT DOCUMENTS 4,124,705  11/1978  Rothman et al. .................... 424/180
4,795,741  1/1989   Leshchiner et al. .................. 514/21

FOREIGN PATENT DOCUMENTS 086627  6/1983  European Pat. Off. .
0325199 7/1989  European Pat. Off. .
357061  3/1990  European Pat. Off. .
359036  3/1990  European Pat. Off. .
386667  9/1990  European Pat. Off. .
415294  3/1991  European Pat. Off. .

OTHER PUBLICATIONS

Kato et al. "Sustained-Release Properties of Microencapsulated Mitomycin C with Ethylcellulose Infused in the Renal Artery of the Dog", Cancer, vol. 46, Jul. 1980, pp. 14–21.
Dakhil et al. "Improved Regional Selectivity of Hepatic Arterial B CNU with Degradable Microspheres" Cancer, vol. 50, Aug. 1982, pp. 631–635.
T. Kanamaru, Chemcial Abstracts, 114(12): 108951x.
Japanese Unexamined Patent Publication No. 97558/1987, Derwent Abstract attached.
Japanese unexamined Patent Publication No. 255231/1988, Derwent Abstract attached.
Japanese Unexamined Patent Publication No. 228910/1989, Derwent Abstract attached.

Primary Examiner—Nutter Nathan M.
Attorney, Agent, or Firm—David G. Conlin; David S. Resnick

[57] ABSTRACT

The present invention relates to an intravascular embolizing agent containing an angiogenesis-inhibiting substance and an intravascular embolizing substance. The agent strengthens the antitumor effect of an angiogenesis-inhibiting substance and serves to reduce the dose and undesirable side effects. And use of the agent in concert with an anti-neoplastic agent brings about further strong and long-lasting antitumor effects.

19 Claims, No Drawings

INTRAVASCULAR EMBOLIZING AGENT CONTAINING ANGIOGENESIS-INHIBITING SUBSTANCE

BACKGROUND OF THE INVENTION

This invention relates to a therapeutic agent for the treatment of cancer which forms emboli in the vascular system surrounding the cancer lesion or tumor. The agent comprises an intravascular embolizing substance and an angiogenesis-inhibiting substance.

Embolization techniques have been utilized, especially for the treatment of inoperable or unresectable tumors. For example, embolization has been used to occlude the nutrient artery feeding the tumor, by administering an intravascular embolizing agent. Chemoembolization techniques have also been utilized. In this case, anti-neoplastic agent in combination with an intravascular embolizing agent have been administered to maintain the concentration of the anti-neoplastic agent high in tumors or cancers.

As intravascular embolizing agents to be used for the above-mentioned purpose, there have been known degradable starch microspheres (DSM) (Cancer, 50, 631 (1982)), lipiodol (Cancer Res., 44, 2115 (1984), crosslinked collagen fibers (Cancer, 46, 14 (1980)), ethyl cellulose microcapsules (Cancer, 46, 14 (1980)), among others.

In these therapeutic methods, however, even the tumor-dominating artery is occluded, since the tumor regenerates by the formation of collateral artery caused by secretion of the tumor-induced angiogenesis factor, there is a fear that satisfactory cancer-suppressive effect would not be expected. Circumstances being such as above, the present inventors have tried to develop an intravascular embolizing agent containing an angiogenesis-inhibiting substance, which is capable of further improving the therapeutic effect by embolization.

The object of this invention is to provide an intravascular embolizing agent which is characterized by containing an angiogenesis-inhibiting substance and an intravascular embolizing substance, and is capable of enhancing cancer-suppressive effects caused by embolization. The present invention provides an intravascular embolizing agent to be administered singly or, in combination with an anti-neoplastic agent, which brings about stronger cancer-suppressive effects.

It has further been unexpectedly found that the cancer-suppressive effect could be enhanced by having an angiogenesis-inhibiting substance included in an intravascular embolizing agent, in a dosage less than that of single administration of an angiogenesis-inhibiting substance.

SUMMARY OF THE INVENTION

The present invention is to provide an intravascular embolizing agent containing an angiogenesis-inhibiting substance and an intravascular embolizing substance.

The agent, with the administration of a relatively small dosage amount, enhances the anti-tumor effect of the angiogenesis-inhibiting substances. The addition of small doses of angiogenesis inhibiting substances also enhances the anti-tumor effect of intravascular embolizing agents.

DESCRIPTION OF THE PREFERRED EMBODIMENT

The angiogenesis-inhibiting substance used in the present invention means a substance performing angiogenesis inhibitory action. For example, it may perform inhibitory action in any of the steps of the following angiogenesis mechanism.

1) Angiogenesis factor is secreted or exuded in the tissue where tumor exists.
2) Angiogenesis factor increases the activities of proteases in endothelial cells of blood vessel, such as plasminogen activator, plasmin, collagenase, etc.
3) Activated protease decomposes the basement membrane surrounding blood vessels.
4) Endothelial cells emigrate toward angiogenesis factors, and they proliferate at the backside of the blood vessels. Endothelial cells form a capillarylike tube arranged lengthwise.
5) Resulting vascular sprouts are connected and form a loop.
6) Blood flows in the loops.
7) Pericytes are observed outside the blood vessels, forming new basement membrane.

The angiogenesis-inhibiting substance means the substance which does not act directly on tumor cells but suppresses tumor growth by inhibiting angiogenesis of tumors, e.g., inhibiting growth of the blood vessels necessary to support solid tumors. The angiogenesis-inhibiting substance thus has an action different from that of conventional anti-tumor agents (Nature, 348, 555 (1990)).

Examples of angiogenesis-inhibiting substances include extracts from cartilage tissue showing collagenase-inhibiting activity (Science, 22, 1185 (1983)), protamine (Nature, 297, 307 (1982)), angiostatic steroid (Science, 221, 719 (1983)), protein, obtained from retinal pigment epithelial cells (Arch. Ophthalmol., 103, 1870 (1985)), anti-cancer factor induced from cultured cartilage cells (Protein, Nucleic Acid and Enzyme, 33, 1803 (1988), anti-inflammatory drugs such as indomethacin (Anticancer Res., 6, 251 (1986)), ribonuclease inhibitors (Proc. Natl. Acad. Sci. U.S.A., 84, 2238 (1987)), drugs exerting influence on collagen metabolism (Biochem. Biophys. Res. Commun., 133, 911 (1985) and Lab. Invest., 59, 44 (1988)), complexes of sulfuric polysaccharide and peptide glycan (cf. e.g. JPA-S63(1988)-119500), gold preparations for rheumatism, herbimycin A (JPA-S63(1988)-295509), and fumagillin produced by microorganisms (cf. e.g. JPA-H1(1989)-279828) or fumagillol derivatives chemically synthesized (EP-A No. 359036, EP-A No. 357061, EP-A No. 86667 or EP-A No. 415294).

Among these, fumagillol derivatives are preferable, for example, fumagillol derivatives represented by the general formula (I)

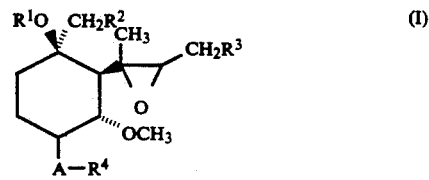

wherein $R^1$ stands for hydrogen, $R^2$ stands for halogen, $N(O)mR^5R^6$, $N^+R^5R^6R^7 \cdot X^-$, $S(O)nR^5$ or $S^+R^5R^6 \cdot X^-$ (wherein $R^5$, $R^6$ and $R^7$ respectively stand for optionally substituted hydrocarbon residues or heterocyclic groups, $X^-$ stands for counter anion, m denotes an integer of 0 or 1, n denotes an integer of 0 to 2, and, $R^5$ and $R^6$ may form N-containing or S-containing heterocyclic rings which may form fused ring together with adjacent nitrogen atom or sulfur atom, and these heterocyclic rings may have substituents), or $R^1$, together with $R^2$, shows a bond, $R^3$ stands for 2-methyl-1-propenyl group or isobutyl group, A stands for O or $NR^8$ (wherein $R^8$ stands for hydrogen or an optionally substituted lower alkyl or aryl group), $R^4$ stands for hydrogen, optionally substituted hydrocarbon residue or an optionally substituted acyl group] are especially preferable.

In the above general formula (I), as the halogen shown by $R^2$, fluorine, chlorine, bromine and iodine are mentioned. And, when a bond is formed with $R^1$ and $R^2$, an epoxy ring is formed.

Examples of the hydrocarbon residues of the optionally substituted hydrocarbon residues shown by $R^5$, $R^6$ or $R^7$ include straight-chain or branched $C_{1-6}$ alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkynyl groups (e.g. ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.) $C_{7-13}$ aralkyl groups (e.g. benzyl, 1-phenethyl, 2-phenethyl, etc.), and $C_{6-10}$ aryl groups (phenyl, naphthyl, etc.).

Examples of the heterocyclic ring of the optionally substituted heterocyclic ring shown by $R^5$, $R^6$ or $R^7$ include 5- or 6-membered heterocyclic groups containing 1 to 4 hetero-atoms (e.g. nitrogen, oxygen, sulfur, etc.) (e.g. 2-furyl, 2-thienyl, 4-thiazolyl, 4-imidazolyl, 4-pyridyl, 1,3,4-thiadiazol-2-yl, 1-methyl-5-tetrazolyl, etc.), and the said heterocyclic groups may further be condensed with a 5- or 6-membered cyclic group (e.g. benzene, pyridine, cyclohexane, etc.) to form a bicyclic fused ring groups (e.g. 8-quinolyl, 8-purinyl, etc.).

Examples of the nitrogen containing heterocyclic group which may be formed by $R^5$ and $R^6$ together with the adjacent nitrogen atom include 4- to 7-membered nitrogen-containing heterocyclic groups (e.g. pyrrolidin-1-yl, piperazino, morpholino, 4-methylpiperazin-1-yl, etc.).

Examples of the sulfur-containing heterocyclic group which may be formed by $R^5$ and $R^6$ together with the adjacent sulfur atom include 4- to 7-membered sulfur-containing heterocyclic groups (e.g. tetrahydrothiophen-1-yl, 1,4-thioxan-1-yl, etc.).

The nitrogen-containing or sulfur-containing heterocyclic group, which may be formed by $R^5$ and $R^6$ together with the adjacent nitrogen atom or sulfur atom, may be fused with a 5- or 6-membered cyclic group (e.g. benzene, pyridine, pyrazine, pyridazine, cyclohexane, etc.) to form a bicyclic fused ring group (e.g. isoindolin-2-yl, 2-isoquinolyl, 1,3-dihydrobenzo[c]thiophen-2-yl, 2,3-dihydrobenzo[b]thiophen-1-yl, 3,4-dihydro-1H-2-benzopyran-2-yl, 3,4-dihdyro-2H-1-benzopyran-1-yl, 1,2,4,5-tetrahydro-3-benzothiepin-3-yl, 1,3-dihydrothieno[3,4-c]pyridin-2-yl, 5,7-dihydrothieno[3,4-b]pyrazin-6-yl, 5,7-dihydrothieno[3,4-d]pyridazin-6-yl, etc.).

Examples of the lower alkyl group of the optionally substituted lower alkyl group shown by $R^8$ include $C_{1-6}$ alkyl groups (e.g. methyl, ethyl, propyl, isopropyl, butyl, isobutyl, sec-butyl, pentyl, isopentyl, hexyl, etc.).

Examples of the aryl group of the optionally substituted aryl group shown by $R^8$ include $C_{6-10}$ aryl groups (e.g. phenyl, naphthyl, etc.).

Examples of the optionally substituted hydrocarbon residue shown by $R^4$ include optionally substituted hydrocarbon residues described in detail as those shown by $R^5$, $R^6$ and $R^7$.

Incidentally, when the hydrocarbon residue shown by $R^4$ is an alkenyl group, it is preferably unsubstituted.

Examples of the optionally substituted acyl group shown by $R^4$ include residues of acids as exemplified by optionally substituted carboxylic acid acyl, sulfonic acid acyl, carbamoyl, thiocarbamoyl or sulfamoyl. More specifically, they are optionally substituted alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, among others.

Examples of the alkanoyl group of the above-mentioned optionally substituted alkanoyl include $C_{1-6}$ alkanoyl groups (e.g. formyl, acetyl, propionyl, isopropionyl, butyryl, pentanoyl, hexanoyl, etc.).

Examples of the aroyl group of the optionally substituted aroyl include $C_{7-11}$ aroyl groups (e.g. benzoyl, 1-naphthoyl, 2-naphthoyl, etc.).

Examples of the heterocyclic carbonyl group of the optionally substituted heterocyclic carbonyl include 5- or 6-membered heterocyclic carbonyl groups (e.g. 2-furoyl, 2-thenoyl, nicotinyl, isonicotinyl, etc.) containing 1 to 4 hetero-atoms (e.g. nitrogen, oxygen, sulfur, etc.).

Examples of the arylsulfonyl group of the optionally substituted arylsulfonyl include $C_{6-10}$ arylsulfonyl groups (e.g. benzenesulfonyl, 1-naphthylsulfonyl, 2-naphthylsulfonyl, etc.).

Examples of the alkylsulfonyl group of the optionally substituted alkylsulfonyl include $C_{1-6}$ alkylsulfonyl groups (methylsulfonyl, ethylsulfonyl, etc.).

Examples of the alkoxycarbonyl group of the optionally substituted alkoxycarbonyl include $C_{2-7}$ alkoxycarbonyl groups (e.g. methoxycarbonyl, ethoxycarbonyl, isobutoxycarbonyl, etc.).

Examples of the aryloxycarbonyl group of the optionally substituted aryloxycarbonyl include $C_{7-11}$ aryloxycarbonyl groups (e.g. phenoxycarbonyl, 1-naphthyloxycarbonyl, 2-naphthyloxycarbonyl, etc.).

Optionally substituted hydrocarbon residues or heterocyclic groups respectively shown by $R^5$, $R^6$ or $R^7$; nitrogen-containing or sulfur-containing heterocyclic groups which are optionally formed by $R^5$ and $R^6$ together with the adjacent nitrogen atom or sulfur atom or which are optionally fused; optionally substituted lower alkyl groups or aryl groups respectively shown by $R^8$ and optionally substituted hydrocarbon residues; or acyl group (alkanoyl group, aroyl group, heterocyclic carbonyl group, carbamoyl group, thiocarbamoyl group, arylsulfonyl group, alkylsulfonyl group, sulfamoyl group, alkoxycarbonyl group or aryloxycarbonyl group) respectively shown by $R^4$ may have optionally 1-3 substituents at positions where such substitution possibly takes place.

Examples of such substituents which may be used to produce the "optionally substituted residues" discussed above include $C_{1-6}$ alkyl groups (e.g. methyl, ethyl, propyl, isopropyl, butyl, isobutyl, sec-butyl, pentyl, isopentyl, hexyl, etc.), $C_{2-6}$ alkenyl groups (e.g. vinyl, allyl, 2-butenyl, methylallyl, 3-butenyl, 2-pentenyl, 4-pentenyl, 5-hexenyl, etc.), $C_{2-6}$ alkynyl groups (e.g. ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (e.g. cyclopropyl, cyclobutyl, cyclopentyl, cyclohexyl, etc.), $C_{3-6}$ cycloalkenyl groups (e.g. cyclobutenyl, cyclopentenyl, cyclohexenyl, cyclohexadienyl, etc.), $C_{6-10}$ aryl groups (e.g. phenyl, naphthyl, etc.), amino, $C_{1-6}$ alkylamino groups (e.g. methylamino, ethylamino, isopropylamino, etc.), di-$C_{1-6}$ alkylamino groups (e.g. dimethylamino, diethylamino, etc.), azido, nitro, halogen (e.g. fluorine, chlorine, bromine, iodine, etc.), hydroxyl, $C_{1-4}$ alkoxy groups (e.g. methoxy, ethoxy, etc.), $C_{6-10}$ aryloxy groups (e.g. phenoxy, naphthyloxy, etc.), $C_{1-6}$ alkylthio groups (e.g. methylthio, ethylthio, propylthio, etc.), $C_{6-10}$ arylthio groups (e.g. phenylthio, naphthylthio, etc.), cyano, carbamoyl group, carboxyl group, $C_{1-4}$ alkoxycarbonyl groups (e.g. methoxycarbonyl, ethoxycarbonyl, etc.), $C_{7-11}$ aryloxycarbonyl groups (e.g. phenoxycarbonyl, 1-naphthyloxycarbonyl, 2-naphthyloxycarbonyl, etc.), carboxy-$C_{1-4}$ alkoxy groups (e.g. carboxymethoxy, 2-carboxyethoxy, etc.), $C_{1-6}$ alkanoyl groups (e.g. formyl, acetyl, propionyl, isopropionyl, butyryl, pentanoyl, hexanoyl, etc.), $C_{7-11}$ aroyl groups (e.g. benzoyl, 1-naphthoyl, 2-naphthoyl, etc.), $C_{6-10}$ arylsulfonyl groups (e.g. benzenesulfonyl, 1-naphthylsulfonyl, 2-naphthylsulfonyl, etc.), $C_{1-6}$ alkylsulfinyl groups (e.g. methylsulfinyl., ethylsulfinyl, etc.), $C_{6-10}$ arylsulfinyl groups (e.g. benzenesulfinyl, 1-naphthylsulfinyl, 2-naphtylsulfinyl, etc.), $C_{1-6}$ alkylsulfonyl groups (e.g. methylsulfonyl, ethylsulfonyl, etc.), 5- or 6-membered heterocyclic groups containing 1-4 hetero-atoms (e.g. nitrogen, oxygen, sulfur, etc.) (e.g. 2-furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl groups containing 1-4 hetero-atoms (e.g. nitrogen, oxygen, sulfur, etc.) (e.g. 2-furoyl, 2-thenoyl, nicotinyl, isonicotinyl, etc.), and 5- or 6-membered heterocyclic thio groups containing 1-4 hetero-atoms (e.g. nitrogen, oxygen, sulfur, etc.) (e.g. 4-pyridylthio, 2-pyrimidylthio, 1,3,4-thiadiazol-2-ylthio, 1-methyl-5-tetrazolylthio, etc.), and, in these heterocyclic thio groups, the benzene ring may optionally be fused to form bicyclic fused-ring thio groups (e.g. 2-benzothiazolylthio, 8-quinolylthio, etc.).

And, when $R^4$ stands for respectively di-substituted carbamoyl group, thiocarbamoyl group or sulfamoyl group, these groups may optionally form nitrogen-containing heterocyclic groups (e.g. pyrrolidin-1-yl, piperidino, morpholino, piperazin-1-yl, 4-methylpiperazin-1-yl, 4-phenylpiperazin-1-yl, etc.) together with the nitrogen atom of the carbamoyl group, thiocarbamoyl group or sulfamoyl group.

The above-mentioned substituents (hereinafter abbreviated as substituents A) at the respectively optionally substituted hydrocarbon residues or heterocyclic groups shown by $R^5$, $R^6$ or $R^7$; the substituents at the nitrogen-containing or the sulfur-containing heterocyclic groups which may optionally be formed by $R^5$ and $R^6$ together with the adjacent nitrogen atom or sulfur atom or which may optionally be in the form of fused ring; the substituents at the respectively optionally substituted lower alkyl groups or aryl groups shown by $R^8$ and the substituents at the respectively optionally substituted hydrocarbon residues; alkanoyl group, aroyl group, heterocyclic carbonyl group, carbamoyl group, thiocarbamoyl group, arylsulfonyl group, alkylsulfonyl group, sulfamoyl group, alkoxycarbonyl group or aryloxycarbonyl group shown by $R^4$ may further be substituted with optionally up to 3 substituents where such residues can accommodate such substitution, and preferably have no substituent or one substituent chosen from the substituents listed above.

These substituents may be elected among the concrete above-mentioned examples of the substituents A.

Examples of the counter anion shown by $X^-$ include halogen ion (e.g. iodide ion, bromide ion, chloride ion, etc.), sulfate ion, phosphate ion, nitrate ion, perchlorate ion, tetrafluoroborate ion, methanesulfate ion, p-tolylsulfate ion, benzenesulfate ion, hydroxyl ion, carboxylate ion of organic acids (e.g. oxalate ion, maleate ion, fumarate ion, succinate ion, citrate ion, lactate ion, trifluoroacetate ion, lactobionate ion, acetate ion, propionate ion, tartrate ion, ethyl succinate ion, etc.).

While the compound (I) has asymmetric center in the molecule and has optical activity, its absolute structure is based on the starting fumagillol, and, unless specifically stated, the absolute structure is in agreement with that of fumagillol. In the bonding mode of substituents on the cyclohexane ring, shows α-linkage, shows β-linkage and — shows either α-linkage or β-linkage.

And, in the case where the compound (I) has, in the molecule, di-lower alkylamino group, nitrogen-containing heterocyclic group or nitrogen-containing aromatic heterocyclic group, the nitrogen atom in these substituents may further be alkylated to form quaternary ammonio group (trimethylammonio, N-methylpyridinio, N-methylpyrrolidin-1-ylium, etc.), and examples of counter anion are the same as those shown by $X^-$ described in the foregoing.

In the compound (I), it is preferable that $R^1$ and $R^2$ form a bonding hand or $R^1$ is hydrogen and $R^2$ is $N(O)mR^1R^2$, $N^+R^1R^2R^3 \cdot X^-$, $S(O)nR^1$ and $S^+(O)mR^1R^2 \cdot X^-$, especially, in $S^+R^1R^2 \cdot X^-$, it is preferable that $R^5$ and $R^6$ are hydrocarbon residues and $X^-$ is halogen.

Preferable example of A is O or NH, a preferred example of $R^3$ is 2-methyl-1-propenyl, and a preferred example of $R^4$ is carbamoyl or ureido.

The compound represented by the general formula (I) can be produced by using, as the starting material, fumagillol which is the hydrolyzate of fumagillin produced by microorganisms [Tarbell, D. S. et al., J. Am. Chem. Soc. 83, 3096 (1961)], and the method of producing the compound (I) and the physico-chemical and biological properties of the compound (I) are described in detail in the above-mentioned official gazette (EP-A No. 359036, EP-A No. 357061, EP-A No. 386667 or EP-A No. 415294). Among those compounds, 6-O-(N-chloroacetylcarbamoyl)fumagillol, 6-O-(N-chloroacetylcarbamoyl)-4′,5′-dihydrofumagillol, 6α-(N′-chloroacetylureido)-6-desoxyfumagillol, 4-(N-chloroacetylcarbamoyloxy)-2-(1,2-epoxy-1,5-dimethyl-4-hexenyl)-1-(1,3-dihydrobenzo[c]thiophen-2-ylio)-methyl-3-methoxycyclohexanol chloride, 4-(N′-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride, etc. are preferable.

The said angiogenesis-inhibiting substance may optionally form salts, and examples of the salts include salts with inorganic bases, salts with organic bases, salts with inorganic acids, salts with organic acids, salts with basic or acid amino groups, etc. Examples of inorganic bases capable of forming these salts include alkali metal (e.g. sodium, potassium, etc.), alkaline earth metal (e.g. calcium, magnesium, etc.), examples of organic bases include trimethylamine, triethylamine, pyridine, picoline, N,N-dibenzylethylenediamine, ethanolamine, diethanolamine, trishydroxymethylaminomethane, dicyclohexylamine, etc., examples of inorganic acids include hydrochloric acid, hydrobromic acid, sulfuric acid, nitric acid, phosphoric acid, etc., examples of organic acids include formic acid, acetic acid, trifluoroacetic acid, oxalic acid, tartaric acid, fumaric acid, maleic acid, methanesulfonic acid, benzenesulfonic acid, p-toluenesulfonic acid, etc., and examples of basic or acid amino acid include arginine, lysine, ornithine, aspartic acid, glutamic acid, etc.

Preferable examples of the intravasclular embolizing substances to be employed in the present invention include oils, which are conventionally used for preparing injectable preparations, such as castor oil, sesame oil or corn oil, conventional metals such as iron, ferrite, etc., insoluble salts of metals such as barium sulfate, ceramics such as calcium phosphate sinter e.g. hydroxylapatite or calcium triphosphate sinter, wax such as cholesterol, glycerol ester of fatty acid or silicone, etc., activated carbon, or a conventional natural or synthetic polymers as exemplified below, etc. Examples of the polymers include polypeptides, polysaccharides, polyfatty acid ester, poly(amino acids), polyaldehyde, polyvinyl polymer, maleic anhydride polymer, etc.

Furthermore, those polymers may be solidified as they are or cured with a cross-linking agent such as formaldehyde. The solidified polymers can be used as the intravascular embolizing agent of the present invention.

The molecular weight of these polymers varies largely with the kinds of polymers, and with whether or not solidification or insolubilization process of cross-linking or curing is conducted, and, while it is hardly mentioned definitively, it ranges from about 1,000 to 1,000,000, more preferably, from about 2,000 to 800,000.

Examples of the polypeptides include gelatin, collagen, elastin, albumin, hemoglobin, transferrin, globulin, fibrin, fibrinogen, keratin sulfate, etc.

Examples of the polysaccharides include dextran, agarose, pullulan, chitosan, mannan, carrageenan, alginic acid, starch, amylose, amylopectin, pectin, lentinan, hyaluronic acid, hylan, ether cellulose (methyl cellulose, ethyl cellulose, carboxymethyl cellulose, carboxyethyl cellulose, hydroxyethyl cellulose, hydroxypropyl cellulose, etc.).

Examples of the poly-fatty acid esters include, among others, homopolymers or copolymers of lactic acid, glycolic acid, hydroxybutyric acid, malic acid, citric acid, tartaric acid, etc.

As, for example, copolymers of lactic acid—glycolic acid, those having a lactic acid/glycolic acid ratio (molar ratio) of 100/1 to 30/70, more preferably, 100/1 to 40/60 and a molecular weight of 1,000 to 100,000, more preferably, about 2,000 to 80,000.

Examples of the poly(amino acid) includes poly-γ-benzyl-L-glutamic acid, poly-γ-methyl-L-glutamic acid, etc.

Examples of the polyvinyl polymers include homopolymers and copolymers of ethylene, propylene, butadiene, acrylic acid, acrylic acid ester, methacrylic acid, methacrylic acid ester, vinyl acetate, vinyl chloride, vinyl alcohol, vinyl pyrrolidone, vinyl ether, vinyl carbazole, styrene, styrene derivatives, α-cyano acrylic acid ester, acrylamide, divinyl benzene, etc.

Among these, gelatin, albumin, collagen, starch, hyaluronic acid, lactic acid - glycolic acid copolymers, etc., which are polymers dissolving or decomposing gradually in vivo, are preferable.

The intravascular embolizing agent of the present invention, as described in detail in the following, can be administered intraarterially in the state of an oil solution, emulsion or suspension. When the intravascular embolizing agent of the present invention is in the state of an emulsion or suspension, the particle size ranges preferably from 10 to 1000 μm.

According to the present invention, the intravascular embolizing agent may be in the form of a mere mixture of the angiogenesis-inhibiting substance with the above-described intravascular embolizing substance or in the form of an agent prepared by allowing the angiogenesis-inhibiting substance to be included in the inner structure of the intravascular embolizing substance or adsorbed on the surface of the intravascular embolizing substance by a per se known method, the latter is preferable.

For allowing the angiogenesis-inhibiting substance to be adsorbed more strongly, ion-exchange resin may be employed as intravascular embolizing substance. Examples of supporting materials of ion-exchange resin include dextran, agarose, cellulose, polystyrene etc. Examples of anionic type ones include DEAE Sephadex, QAE Sephadex, DEAE Sepharose, DEAE Cellulose, QAE Cellulose and various types of Amberlite-IRA, Dowex-1, etc. Examples of catconic type ones include CM Sephadex, CM Sepharose, CM Cellulose and various types of Amberlite-IR, Dowex-50W. (These examples are all manufactured by Sigma, Inc.)

The agent of the present invention adsorbing the angiogenesis-inhibiting substance on the intravascular embolizing substance can be prepared by mere mixing the ion-exchange resin and the angiogenesis-inhibiting substance.

While the dose of the angiogenesis-inhibiting substance depends on the strength of its pharmacological action, it is not specifically limited so long as it is effective, and the dose at one time is selected from the range of from 50 μg to 2 g, more preferably, from 200 μg to 1 g. In the case of above-mentioned fumagillin derivatives such as 6-0-(N-chloroacetylcarbamoyl)fumagillol and 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride, the dose at one time is selected from 0.5 to 500 mg. In case of the above specific compound, a dose of 500 mg per adult person at one time and the administration of one time one month is quite enough for satisfactory effectiveness. And, while the concentration of the angiogenesis-inhibiting substance depends on the strength of its pharmacological effect, the solubility in water or organic solvent, particle-formability, etc., it ranges desirably from 0.01 to 95 weight % relative to the intravascular embolizing agent, especially from 0.1 to 90 weight %.

For allowing an angiogenesis-inhibiting substance to be included in an intravascular embolizing substance, a number of per se known methods can be used. For example, while described in detail in working examples, when both the intravascular embolizing substance and angiogenesis-inhibiting substance are soluble in an organic solvent, they are dissolved in, for example, dichloromethane, chloroform, ethyl acetate, isopropyl ether, etc., then the solution is dispersed in an aqueous phase containing a surfactant or a protective colloid, or spray-dried to evaporate off the organic solvent to provide microspheres of intravascular embolizing agent. In this case, the angiogenesis-inhibiting substance need not completely be dissolved. As the surfactant or the protective colloid, any one can be employed so long as it is capable of forming stable oil/water emulsion, for example, anionic surfactants (sodium oleate, sodium stearate, sodium lauryl sulfate, etc.), nonionic surfactants (polyoxyethylene sorbitan fatty acid ester, polyoxyethyelne castor oil derivatives, etc.), polyvinyl alcohol, polyvinyl pyrrolidone, carboxymethyl cellulose, lecithin, gelatin, etc can be used. These may be employed singly or in combination of two or more of them. Especially, polyvinyl alcohol, carboxymethyl cellulose and gelatin are preferable. The concentration is selected from the range of 0.01 to 20%, preferable 0.05 to 10%.

For allowing a water-soluble angiogenesis-inhibiting substance to be included in an intravascular embolizing substance soluble in an organic solvent, for example, an aqueous solution of the angiogenesis-inhibiting substance is finely dispersed in a solution of the intravascular embolizing substance in such an organic solvent as mentioned above, then the organic solvent is evaporated to prepare microspheres of intravascular embolizing agent. In this case also, the angiogenesis-inhibiting substance is not required to be completely dissolved.

While the concentration of these intravascular embolizing substances in any of organic solvents is not specifically limited, it should be within the range giving the substance a viscosity enough to be dispersed as fine particles when dispersed in the aqueous phase for desolvation, i.e. the concentration is selected from the range of 1 to 80%, more preferably from 5 to 60%.

For allowing an angiogenesis-inhibiting substance soluble in an organic solvent to be included in a water-soluble intravascular embolizing substance, the angiogenesis-inhibiting substance is dispersed as it is in an aqueous solution of intravascular embolizing substance such as an aqueous solution of albumin, or it is once dissolved in a volatile organic solvent, e.g. isopropyl ether to disperse the organic solvent solution of the angiogenesis-inhibiting substance in the aqueous solution of for example albumin as fine particles, then allowing the above-prepared liquid preparation to be dispersed in an oily phase of e.g. soybean oil or silicone oil, followed by solidification to give microspheres of intravascular embolizing agent. For the solidification, there are known several methods, for example, heating the dispersion at 120° to 160° C. or subjecting the dispersion to cross-linking with, for example, formaldehyde or glutaraldehyde. When said liquid preparation is dispersed in an oily phase, for forming a stable water/oil type emulsion, a surfactant, for example, sorbitan monooleate or sorbitan sesquioleate may be added, and its concentration is selected from the range up to 20%.

Further, in case when both of the substances are soluble in water, both are dissolved in water, then the aqueous solution is dispersed in e.g. the above-mentioned silicone oil phase, followed by the same solidification process as mentioned above to give an intravascular embolizing agent.

In the case of these water-soluble intravascular embolizing substances as well, the concentration is not specifically limited but should be within such a range as giving these substances a viscosity enough to be dispersed as fine particles when dispersed in an oily phase, i.e. the concentration is selected from the range of 1 to 80%, more preferably 2 to 60%.

Use of the intravascular embolizing agent containing the angiogenesis-inhibiting substance and the intravascular embolizing substance of the present invention in concert with an anti-neoplastic agent is more effective. The anti-neoplastic agent may be mixed with, or allowed to be contained in the above-mentioned intravascular embolizing agent.

As the method for the latter case, a per se known method is employed, depending on whether the anti-neoplastic agent is soluble in water or an organic solvent, in the same manner as in the above-described method for allowing a angiogenesis-inhibiting substance to be included in an intravascular embolizing agent. And, in this case, an intravascular embolizing agent containing an intravascular embolizing substance, an angiogenesis-inhibiting substance and an anti-neoplastic agent may be administered, or a mixture of (1) an intravascular embolizing agent containing an intravascular embolizing substance and an angiogenesis-inhibiting substance and (2) an intravascular embolizing agent containing an intravascular embolizing substance and an anti-neoplastic agent may be administered. Examples of the anti-neoplastic agent include alkylating agents such as nitrogen mustard-N-oxide hydrochloride, cyclophosphamide, thio-TEPA, carbocon, chlorambucil, nimustine hydrochloride, ifosfamide, melphalan, dacarbazine, uracil mustard, mannomustine, dopan, BCNU, triethylenemelamine, aza-TEPA, trenimon, isoprocuon, busulfan, dimethyl mirelan, piposulfan, etoglucid, epoxypropidine, epoxypiperazine, hexamethylmelamine, dibromomannitol and pipobroman; metabolic antagonists such as aminopterin, methotrexate, carmofur, guanine, 8-azaguanine, mercaptopurine, thioinosine, azathiopurine, uracil, fluorouracil, tegafur, SITARABIN, ancitabine hydrochloride, enocitabine, azaserine and diazomycin; antibiotics such as actinomycin D, cyclomycin, mitomycin C, daunomycin, daunorubicin hydrochloride, doxorubicin hydrochloride, bleomycin hydrochloride, bleomycin sulfate, neocarzinostatin, peplomycin sulfate, aclarubicin hydrochloride, chromomycin A3, epilubisin hydrochloride, ansamycin, carzinophilin and pyralvicin; plant alkaloids such as vinblastine sulfate, vincristine sulfate, vindesine sulfate and etoposide; platinum complexes such as cisplatin and carboplatin; and others such as Hg-hematoprophyrin, Coprotoporphyrin, procarbazine hydrochloride, estramustine phosphate sodium, ranimustine, mitoxantrone, doxifluridine and L-asparaginase.

While the dose of the anti-neoplastic agent depends on the strength of its pharmacological effect, it is not specifically limited, if only the dose at one time is selected from the range of 50 µg to 2 g. In the case of popular anti-neoplastic agents, such as doxorubicin hydrochloride, cisplatin, mitomycin C, and bleomycin hydrochloride, the dose at one time is selected from 0.1 to 500 mg. And, while the concentration of the anti-neoplastic agent in the intravascular embolizing agent depends on the strength of its pharmacological effect, the solubility in water or organic solvent, particle-formability, etc., it ranges from 0.1 to 90% in the intravascular embolizing agent.

The intravascular embolizing agent of the present invention is used as it is, or by dispersing, before or at the time of use in a proper pharmaceutically acceptable carrier, for example, a dispersing vehicle or a contrast medium such as lipiodol. Examples of the dispersing vehicle include injectable distilled water in which a dispersing agent (e.g. polyoxysorbitan fatty acid ester, carboxymethyl cellulose, etc.), a preservative (e.g. methylparaben, propylparaben, etc.) and an isotonizing agent (e.g. sodium chloride, mannitol, glucose, etc.), or a vegetable oil such as sesame oil, corn oil, etc. The intravascular embolizing agent dispersed thus above is administered through a catheter into tumor-dominating artery from a relevant artery while monitoring with an angiographic agent. In the case of liver cancer, the intravascular embolizing agent is administered selectively as much as practicable at the site of tumor through catheter inserted into hepatic artery from gastroduodenal artery. While the dose varies with the kind, amount, particle size and decomposability of the intravascular embolizing substance; with the kind, site, size of the tumor; and with the kind and amount of the angiogenesis-inhibiting substance, it ranges from 1 mg to 10 g for one time, more preferably from 5 mg to 5 g. In the case of microspheres of lactic acid-glycolic acid copolymer (lactic acid/glycolic acid=75/25 molar ratio, average molecular weight 10500) containing above-mentioned fumagillol derivertives such as 6-O-(N-chloroacetylcarbamoyl)fumagillol and 4-(N'-chloroacetylureido)-2-(1,2-epoxy-1,5-dimethyl-4-hexenyl)-1-(1,3-dihydrobenzo[c]thiophen-2-ylio)methyl-3-methoxycylohexanol chloride, the dose is selected from 10 mg to 2 g.

In case of the above microsphere, a dose of 2g per adult person at one time and the administration of one time one mouth is quite enough for satisfactory effectiveness.

Since the intravascular embolizing agent of the present invention is administered into tumor-dominating artery, the agent is required to satisfy the requirements for conventional injections. Preferable examples of the embolizing agent, while depending on the stability of the constituents, i.e. the intravascular embolizing substance and the angiogenesis-inhibiting substance, include oily preparations containing the angiogenesis-inhibiting substance or those to be dissolved or dispersed at the time of use, or solid or powdery preparations using the afore-mentioned materials and, besides, using biodegradable materials to be dissolved and dispersed at the time of use. And, to this embolizing agent may be added a preservative, stabilizer, isotonizing agent, solubilizer, dispersing agent diluent, etc. conveniently usable for injections. The tumor, to which the intravascular embolizing agent containing the angiogenesis-inhibiting substance of the present invention is applicable, may be any one into the dominating artery of which a catheter can be inserted selectively, irrespective of whether the cancer may be primary or metastatic. At present, tumors to which this chemoembolization is applied most frequently are inoperable hepatic tumors, and the inoperable renal tumors follows. However, in view of the advanced level of medical technique, selective insertion of a catheter into the artery of almost all organs is considered possible ["Douchu Gan Kagaku Ryoho" (Chemotherapy of Tumors by Arterial Injection), under the supervision of Hironobu NAKAMURA and Tetsuo TAGUCHI, published by "Gan To Kagaku Ryoho Sha" (1986)], and this therapeutic method is applied more widely. Therefore, the intravascular embolizing agent of this invention is effective for the chemotherapy by intraarterial injection now often applied to tumors including hepatic tumor, renal tumor, pyelo tumor, pancreatic tumor, urinary bladder tumor, prostatic tumor, breast cancer, stomach cancer, large intestinal tumor, colonic tumor, etc. The intravascular embolizing agent containing the angiogenesis-inhibiting substance of the present invention is useful for the anti-tumor therapy of the warm-blooded animals preferably mammals such as human, monkey, horse, cattle, swine, dog, rabbit, sheep, rat, mouse etc.

WORKING EXAMPLES

The following working examples further illustrate the present invention, but do not intend to limit the scope of the invention.

EXAMPLE 1

45 mg of 6-O-(N-chloroacetylcarbamoyl) fumagillol (hereinafter simply called "Compound a") and 2 g of a lactic acid—glycolic acid copolymer (hereinafter abbreviated as PLGA, lactic acid/glycolic acid=75/25 molar ratio, weight average molecular weight 10500) were dissolved in a mixture of 2 g of dichloromethane and 0.7 g of chloroform. The resultant solution was poured into 400 ml of 0.1 % aqueous solution of polyvinyl alcohol to give an emulsion by the use of a small-sized homogenizer. The organic solvent in this emulsion was volatilized under stirring. The microspheres (hereinafter abbreviated as msp) thus obtained were collected by a centrifuge. The microspheres were again dispersed in distilled water, which was further subjected to centrifuge to remove untrapped chemicals, followed by collecting msp. The msp was subjected to freeze-drying to complete desolvation and dehydration.

EXAMPLE 2

A cell-suspension of $VX_2$ carcinoma was transplanted subcutaneously to male Kbl:JW rabbits at the site under the knee of the right hind leg. These animals were divided into four groups two weeks after the transplantation. Each group of test animals were injected from the upper site of the homolateral femoral artery (i.a.) with a dispersion of 50 mg of polystyrene (hereinafter abbreviated as PS) msp (average particle size:50 $\mu$m) in the solution containing 1 mg of "Compound a", with the same amount of only PS msp suspended in dispersing vehicle, and with the same dose of "Compound a" solution, respectively. On the 5th day after the administration, the volume (major axis x minor axis x height of the tumor) was measured. The volume of the tumors in each group before the administration was assumed as 100%, and the relative values (V5/V0, %) and the volume ratios (T/C, %) relative to the untreated control group were shown by Table 1.

TABLE 1

| Treatment (i.a.) | Number of animals | V5/V0 (%) | T/C (%) |
|---|---|---|---|
| Control | 10 | 227 | 100 |
| "Compound a" | 3 | 175 | 77 |
| PS | 4 | 134 | 59 |
| "Compound a" + PS | 2 | 81 | 36 |

In the intraarterial injection of PS msp without drug or "Compound a" solution, the volume of the tumor was suppressed to 59% or 77% of that in the control group, but 134% or 175% relative to that before treatment, respectively. On the other hand, by the embolization after coadministering intraarterially the angiogenesis-inhibiting agent "Compound a" and PS msp, the volume of the tumor was reduced to 81% of that before administration and suppressed to 36% relative to that of the control group.

EXAMPLE 3

Fifty mg of PLGA msp(msp-1) containing 1 mg of "Compound a" prepared in Example 1, 50 mg of PLGA msp(msp-p) not containing drug, or 1 mg of drug solution was injected each intraarterially to determine the anti-cancer activities similarly as Example 2. On the 7th day after the administration, the tumor volume of that before the administration (V7/V0,%) and volume ratios (T/C,%) relative to the untreated control group were shown in Table 2. And, anti-cancer effects in the group to which the solution containing 1 mg of "Compound a" was administered into auricular vein (i.v.) three times, 0, 2nd and 5th day, were similarly evaluated. Incidentally, particle sizes of msp-1 and msp-p are both 25 to 125 μm.

TABLE 2

| Treatment (i.a.) | Number of animals | V7/V0 (%) | T/C (%) |
|---|---|---|---|
| Control | 10 | 358 | 100 |
| Solution (i.a.) | 3 | 247 | 69 |
| msp-p (i.a.) | 4 | 225 | 63 |
| msp-1 (i.a.) | 5 | 41 | 11 |
| Solution (i.v.) | 2 | 294 | 82 |

In the intraarterial injection of msp-p or drug solution, the volume of the tumor increased to 225% or 247% of that before the embolization, and 63% or 69% relative to that in untreated groups, respectively. On the other hand, by the embolization with msp-1 including the angiogenesis-inhibiting substance, "Compound a", the size of the tumor was reduced to 41% relative to that before administration, and 11% relative to that in untreated group. The T/C value obtained here is about ⅛ of that obtained by intravenous injection of "Compound a" at the total dose of three times as much in embolization, performing remarkable anti-cancer effects, and lowering of side-effects brought by decrease of the dose can be expected.

EXAMPLE 4

Fifty mg of PLGA(msp-2) containing 1.5 mg of 6α-(N'-chloroacetylureido)-6-desoxyfumagillol (hereinafter abbreviated as "Compound b") prepared by substantially the same manner as in Example 1 or the same amount of PLGA msp (msp-p) not containing "Compound b" was injected each intraarterially to determine the anti-cancer effects similarly as Example 2. Results on the 7th day after the administration were shown in Table 3. Incidentally, particle sizes of msp-2 and msp-p are both 25 to 125 μm.

TABLE 3

| Treatment (i.a.) | Number of animals | V7/V0 (%) | T/C (%) |
|---|---|---|---|
| Control | 10 | 358 | 100 |
| msp-p | 4 | 225 | 63 |
| msp-2 | 2 | 31 | 9 |

In the embolization with msp-p, the volume of the tumor was increased to 225% relative to that before the embolization and 63% relative to that of the control group, while, in the embolization with msp-2 containing an angiogenesis-inhibiting substance, "Compound b", the volume of the tumor was reduced to 31% as compared with that before administration and 9% as compared with that in the control group, which was a remarkable effect.

EXAMPLE 5

A dispersion of 50 mg of msp-1 in the aqueous solution of.1 mg of doxorubicin hydrochloride (here in after abbreviated as DOX), a dispersion of 50 mg PLGA msp (msp-3) including 1.23 mg of 4-(N'-chloroacetylureido)-2-(1,2-epoxy-1,5-dimethyl-4-hexenyl)-1-(1,3-dihydrobenzo[c]thiophen-2-ylio)methyl-3-methoxycyclohexanol chloride (hereinafter abbreviated as "Compound c") in the aqueous solution of 1 mg of DOX, a dispersion of 50 mg of msp-p in a similar aqueous solution of DOX, or the above-mentioned aqueous solution of DOX singly was injected each intraarterially to determine the anti-cancer activities similarly as Example 2. On the 5th, 7th and 9th day after the administration, the tumor volume % of that before the administration was shown in Table 4. The particle size of msp-3 is 25 to 125 μm.

TABLE 4

| Treatment (i.a.) | Number of animals | 5th day | 7th day | 9th day |
|---|---|---|---|---|
| Control | 10 | 227 | 358 | 468 |
| DOX | 4 | 162 | 324 | 377 |
| msp-p + DOX | 4 | 70 | 89 | 182 |
| msp-1 + DOX | 5 | 24 | 19 | 23 |
| msp-3 + DOX | 2 | 27 | 20 | 28 |

After intraarterial injection of only DOX solution, the growth of the tumor was inhibited compared with untreated control but the volume of the tumor was not reduced.

In the embolization with coadministration of msp-p and DOX, the volume of the tumor was reduced to 70% on the 5th day and 89% on the 7th day after the administration, relative to that before embolization, but on the 9th day after the administration, the volume of the tumor gained again up to 182% relative to that before embolization. On the contrary, in the embolization by coadministration of DOX and msp-1 or msp-3 containing "Compound a" or "Compound c", the volume was reduced to about 23% and 28%, respectively relative to that before administration even on the 9th day after the administration, maintaining remarkable anti-cancer effects.

EXAMPLE 6

In 4.5 ml of water, were dissolved 70 mg of "Compound c" and 2.9 g of bovine serum albumin (BSA). This solution was added to 80 ml of sesame oil containing 1 ml of sorbitan sesquioleate, then the mixture was made into a water/oil emulsion by using a mechanical mixer. Ten minutes later, 20 ml of sesame oil, in which glutaraldehyde was dissolved to the extent of saturation, was added to the emulsion. The mixture was stirred for 5 hours at room temperature to allow cross-linking reaction to proceed. This emulsion was then subjected to centrifugal separation. Washing was conducted three times by replacing the supernatant with the same volume of isopropyl alcohol, followed by drying under reduced pressure to afford BSA msp (msp-BSA) containing "Compound c".

EXAMPLE 7

Fifty mg each of msp-3 containing the "Compound c" employed in Example 5 and of msp-BSA obtained by Example 6 were administered intraarterially to determine the anti-cancer effects similarly as Example 2. The results on the 7th day after the administration are shown in Table 5. The particle size dry of msp-BSA is 25 to 75 μ.

TABLE 5

| Treatment (i.a.) | Number of animals | V7/V0 (%) | T/C (%) |
|---|---|---|---|
| Control | 16 | 350 | 100 |
| msp-3 | 3 | 59 | 17 |
| msp-BSA | 3 | 50 | 14 |

In the control group, the volume of the tumor increased to 350% on the 7th day after starting the treatment. On the other hand, in the test groups which were respectively administered with msp-3 and msp-BSA, the volumes were reduced to 59% and 50% respectively, corresponding to 17% and 14% respectively relative to the volume of the tumor in the control group.

EXAMPLE 8

One ml of lipidol (hereinafter abbreviated as LPD) in which 1 mg of "Compound a" or "Compound c" was dissolved or dispersed, were administered intraarterially to determine the anti-cancer activities similarly as Example 2. On the 5th day after the administration, the volume of the tumors was measured and the results are shown in Table 6.

TABLE 6

| Treatment (i.a.) | Number of animals | V5/V0 (%) | T/C (%) |
|---|---|---|---|
| Control | 16 | 219 | 100 |
| LPD + "Compound a" | 4 | 86 | 39 |
| LPD + "Compound c" | 3 | 111 | 51 |

In the untreated group, the volume of the tumor increased to 219% on the 5th day after the start of the test. On the other hand, in the test groups which were respectively administered with "Compound a" and LPD, and with "Compound c" and LPD, the volumes were 86% and 111% respectively, corresponding to respectively 39% and 51% of the volume of the tumor in the untreated group, thus remarkable effect of reducing the size of tumors being observed.

The human cancer is effectively treated in the same manner as above

The intravascular embolizing agent containing the angiogenesis-inhibiting substance and the intravascular embolizing substance of the present invention, with the administration of a relatively small dosage amount, enhances the anti-tumor effect of the angiogenesis-inhibiting agent and to reduce the dose and undesirable side effects And, use of the intravascular embolizing agent in concert with an anti-neoplastic agent shows further strong and long-lasting antitumor effect, thus the agent is remarkably useful a chemo-embolizing agent against malignant tumors.

What we claim is:

1. An intravascular embolizing agent containing an angiogenesis-inhibiting substance and an intravascular embolizing substance, said agent being in the state of an oil solution, an emulsion or a suspension.

2. An intravascular embolizing agent as claimed in claim 1 being in the state of an emulsion or suspension containing granules whose size ranges from 10 to 1000 μm.

3. An intravascular embolizing agent as claimed in claim 1 wherein the angiogenesis-inhibiting substance is a fumagillol derivative.

4. An intravascular embolizing agent as claimed in claim 1 wherein the angiogenesis-inhibiting substance is 6-O-(N-chloroacetylcarbamoyl)fumagillol.

5. An intravascular embolizing agent as claimed in claim 1 wherein the angiogenesis-inhibiting substance is 6α-(N'-chloroacetylureido)-6-desoxy fumagillol.

6. An intravascular embolizing agent as claimed in claim 1 wherein the angiogenesis-inhibiting substance is 4-(N'-chloroacetyluredio)-2-(1,2-epoxy-1,5-dimethyl-4-hexenyl)-1-(1,3-dihydrobenzo[c]thiophene-2-ylio)methyl-3-methoxycyclohexanol chloride.

7. An intravascular embolizing agent as claimed in claim 1 characterized by having the angiogenesis-inhibiting substance included in the intravascular embolizing substance.

8. An intravascular embolizing agent as claimed in claim 1 characterized by that the angiogenesis-inhibiting substance is adsorbed on the intravascular embolizing substance.

9. An intravascular embolizing agent as claimed in claim 1 wherein the intravascular embolizing substance is an oil, a metal, an insoluble salt of metal, a ceramic, wax, activated carbon, polypeptide, polysaccharide, hydroxycarboxylic acid polymer, polyamino acid, polyaldehyde, polyvinyl polymer or maleic anhydride polymer.

10. An intravascular embolizing agent as claimed in claim 1 wherein the intravascular embolizing substance is a polymer which gradually dissolves or decomposes in a living body.

11. An intravascular embolizing agent as claimed in claim 1 wherein the intravascular embolizing substance is gelatin, albumin, collagen, starch hyaluronic acid or lactic acid-glycolic acid copolymer.

12. An intravascular embolizing agent as claimed in claim 1 wherein the intravascular embolizing substance is a lactic acid-glycolic acid copolymer whose molar ratio of lactic acid and glycolic acid is in the range of 100/1 to 30/70 and molecular weight ranges from 1,000 to 100,000.

13. An intravascular embolizing agent as claimed in claim 1 wherein the angiogenesis-inhibiting substance is a fumagillol derivative and the intravascular embolizing substance is a lactic acid-glycolic acid copolymer.

14. An intravascular embolizing agent as claimed in claim 1 wherein the angiogenesis-inhibiting substance is 6-O-(N-chloroacetylcarbamoyl)fumagillol and the intravascular embolizing substance is a lactic acid-glycolic acid copolymer.

15. An intravascular embolizing agent as claimed in claim 1 wherein the angiogenesis-inhibiting substance is 6α-(N'-chloroacetylureido)-6-desoxy fumagillol and the intravascular embolizing substance is a lactic acid-glycolic acid copolymer.

16. An intravascular embolizing agent as claimed in claim 1 wherein the angiogenesis-inhibiting substance is 4-(N'-chloroacetyluredio)-2-(1,2-epoxy-1,5-dimethyl-4-hexenyl)-1-(1,3-dihydrobenzo[c]thiophene-2-ylio)-methyl-3-methoxycyclohexanol chloride and the intravascular embolizing substance is lactic acid-glycolic acid copolymer.

17. An intravascular embolizing agent as claimed in claim 1 characterized by the agent further contains an anti-neoplastic agent.

18. A pharmaceutically acceptable composition which comprises an intravascular embolizing agent as claimed in claim 1 and a pharmaceutically acceptable carrier.

19. A method for suppressing cancer comprising administering an effective amount of an intravascular embolizing agent as claimed in claim 1 optionally together with a pharmaceutically acceptable carrier.

* * * * *